(12) United States Patent
King et al.

(10) Patent No.: US 12,016,678 B2
(45) Date of Patent: Jun. 25, 2024

(54) METHODS AND APPARATUS FOR VISUALISING A PRINT ON AN OBJECT

(71) Applicant: THE SECRETARY OF STATE FOR DEFENCE, Salisbury (GB)

(72) Inventors: Roberto Stefano Pasquale King, Loughborough (GB); Paul Francis Kelly, Loughborough (GB); Steven Geoffrey Thorngate, Salisbury (GB)

(73) Assignee: The Secretary of State for Defence, Salisbury (GB)

( * ) Notice: Subject to any disclaimer, the term of this patent is extended or adjusted under 35 U.S.C. 154(b) by 1324 days.

(21) Appl. No.: 16/492,704

(22) PCT Filed: Mar. 14, 2018

(86) PCT No.: PCT/GB2018/000040
§ 371 (c)(1),
(2) Date: Sep. 10, 2019

(87) PCT Pub. No.: WO2018/167454
PCT Pub. Date: Sep. 20, 2018

(65) Prior Publication Data
US 2020/0046266 A1    Feb. 13, 2020

(30) Foreign Application Priority Data

Mar. 14, 2017 (GB) .................. 1704052

(51) Int. Cl.
*A61B 5/1172* (2016.01)
*C01B 21/086* (2006.01)
(Continued)

(52) U.S. Cl.
CPC .......... *A61B 5/1172* (2013.01); *C01B 21/086* (2013.01); *C01B 21/0865* (2013.01);
(Continued)

(58) Field of Classification Search
CPC .................................. A61B 5/1172
See application file for complete search history.

(56) References Cited

U.S. PATENT DOCUMENTS

2006/0194850 A1    8/2006   Yamamoto et al.

FOREIGN PATENT DOCUMENTS

GB        2038297 A    7/1980
GB        2207791 A    2/1989

OTHER PUBLICATIONS

Thewalt et al., S4N4 und seine Derviate: Darstellung, Struktur and Thermolyse von CuBr—S4N4, 1982, . Naturforsch, 37B, pp. 828-831 (Year: 1982).*

(Continued)

*Primary Examiner* — Dah-Wei D. Yuan
*Assistant Examiner* — Andrew J Bowman
(74) *Attorney, Agent, or Firm* — Kilpatrick Townsend & Stockton LLP (57) ABSTRACT

The present invention provides a method for the production of a metal halide adduct of $S_4N_4$, in particular a specific copper adduct of $S_4N_4$, for the visualisation of a print on an object, in particular a fingerprint on a metal object. The present invention also provides a method and apparatus for visualising a print on an object, using $S_2N_2$ obtained from a metal halide adduct of $S_4N_4$.

19 Claims, 2 Drawing Sheets

(51) Int. Cl.
  *C01B 25/234* (2006.01)
  *G06V 40/12* (2022.01)
  *G06V 40/13* (2022.01)

(52) U.S. Cl.
  CPC ........ *C01B 25/234* (2013.01); *G06V 40/1306* (2022.01); *G06V 40/1365* (2022.01)

(56) References Cited

OTHER PUBLICATIONS

Kelly et al., Fingerprint and inkjet-trace imaging using disulfur dintride, 2008, ChemComm, pp. 6111-6113 (Year: 2008).*
R1, Inorganic Seminar Abstracts, 1965, Library of the University of Illinois, pp. 1-466 (Year: 1965).*
Coucouvanis et al., Inorganic Synthesis, 2002, University of Michigan, vol. 33, pp. 1-299 (Year: 2002).*
Alange et al., "Adducts of Tetrasulphur Tetranitride," Journal of Inorganic Nuclear Chemistry, 1978, pp. 203-210, vol. 40, Pergamon Press, Great Britain.
Ashley et al., "Infrared spectra of adducts of tetrasulfur tetranitride with metal halides," Canadian Journal of Chemistry, Jul. 15, 1969, pp. 2587-2591, vol. 47, No. 14, Canadian Science Publishing, Canada.
Bleay et al., "Polymerisation of S2N2 to (SN)x as a tool for the rapid imaging of fingerprints removed from metal surfaces," Journal of Materials Chemistry, 2010, pp. 10100-10102, vol. 20, The Royal Society of Chemistry, Great Britain.
Kelly et al., "Fingerprint and inkjet-trace imaging using disulfur dinitride," Chem. Commun., 2008, pp. 6111-6113, vol. 46, Royal Society of Chemistry, Great Britain.
Kelly et al., "The use of sulfur nitrides as fingerprint developers," Proceedings of SPIE, 2009 pp. 748602-1-748602-10, vol. 7486, International Society for Optical Engineering.
King et al., "Rapid polymerisation of S2N2 within Na-ZSM-5 channels," Chem. Commun., 2007, pp. 4812-4814, vol. 45, The Royal Society of Chemistry, Great Britain.
Roesky et al., "Crystal and molecular structure of bis-tetrasulphurtetranitride-tetrachlorotin," Zeitschrift fur Kristallographie, 1983, pp. 123-127, vol. 163, Akademische Verlagsgesellschaft, Germany.
Thewalt et al., "S4N4 Bridge Ligand: Structure of CuCl—S4N4," Angewandte Chemie, Dec. 1976, pp. 807-808, vol. 88, No. 23, Wiley-VCH on behalf of the German Chemical Society, Germany.
Thewalt et al., "S4N4 und seine Derivate: Darstellung, Strucktur und Thermolyse von CuBr—S4N4," Zeitschrift fur Naturforschung—Section B Journal of Chemical Sciences, 1982, pp. 828-831, vol. 37, No. 7, Walter de Gruyter GmbH, Germany.
Villena-Blanco et al., "Chapter VI: 25. Tetrasulfur Tetranitride, S4N4," Inorganic Syntheses, 1967, pp. 98-102, McGraw-Hill Book Company, Inc.
United Kingdom Patent Application No. GB1704052.8, Search Report dated Apr. 18, 2018, 2 pages.
United Kingdom Patent Application No. GB1804040.2, Combined Search and Examination Report dated Aug. 21, 2018, 6 pages.
International Patent Application No. PCT/GB2018/000040, International Search Report and Written Opinion dated Oct. 17, 2018, 20 pages.
Chinese Patent Application No. 201880017913.0, Office Action dated Jul. 4, 2022, 13 pages.
Tyree Jr., "Inorganic Syntheses, vol. IX, Chapter VI," Jan. 1, 1967, pp. 98-101, McGraw-Hill Book Company, Inc.
International Patent Application No. PCT/GB2018/000040, International Preliminary Report on Patentability dated Sep. 26, 2019, 14 pages.

* cited by examiner

METHODS AND APPARATUS FOR VISUALISING A PRINT ON AN OBJECT

The invention relates to a method for the production of a metal halide adduct of tetrasulfur tetranitride, $S_4N_4$, for the visualisation of a print on an object, particularly a fingerprint such as a latent fingerprint, and an associated method for visualising a print on an object. The invention also relates to an apparatus for implementing the method for visualising a print on an object.

The use of prints in solving crimes is still of high importance. Since the late nineteenth century, fingerprint identification methods have been used by police agencies around the world to identify suspected criminals. The basis of the traditional fingerprinting technique is based on the observation that the skin on the palmar surface of the hands and feet forms ridges, so-called papillary ridges, in patterns that are unique to each individual and which do not change over time.

There are three different types of fingerprints: visible, impression, and latent. Visible prints are also called patent prints and are left in some medium, like blood or ink that reveals them to the naked eye. They can occur, for example, when blood, dirt, ink or grease on a finger come into contact with a smooth surface of an object and leave a friction ridge impression that is visible without development. Impression prints are also called plastic prints and are indentations left in soft pliable material, for example clay, wax and paint, which will take the impression. They are visible and often can be viewed or photographed without development. Latent prints are not apparent to the naked eye. They are formed from the sweat from sebaceous glands on the body or water, salt, amino acids and oils contained in sweat. The sweat and fluids create prints that must be developed before they can be seen or photographed.

Investigators normally need a portable, permanent copy of the fingerprints. A photograph can generally fulfil this need. Of the three types of fingerprints, visible fingerprints can be photographed directly, and impression fingerprints can usually be photographed under special lighting conditions, but invisible latent fingerprints are difficult to photograph. They must first be made visible.

Ways to render latent fingerprints visible, so that it is possible to photograph such prints, can be complex and may depend, for example, on the type of objects on which they have been left. It is generally necessary to use a 'developer', usually a powder or chemical reagent, to produce a high degree of visual contrast between the ridge patterns and the object on which a fingerprint has been deposited.

Developing agents often depend on the presence of organic materials or inorganic salts for their effectiveness, although the water deposited may also take a key role. Fingerprints are typically formed from the aqueous-based secretions of the eccrine glands of the fingers and palms with additional material from sebaceous glands primarily from the forehead. This latter contamination results from the common human behaviors of touching the face and hair.

Examples of techniques which use developing agents include techniques using ninhydrin or diazafluorenone, vacuum metal deposition and ethyl cyanoacrylate polymerisation. Other methods, such as the application of fine powders, work by adhesion to sebaceous deposits and possibly aqueous deposits in the case of fresh fingerprints.

The choice of imaging agent is predominantly determined by the object composition and the environmental events experienced, such as wetting, heat and friction. Chemical treatment methods such as those described above typically rely on the reaction of one, or more, fingerprint constituents with the working chemical. For example, ninhydrin requires the presence of amine to produce a visible print, while diazafluoren-9-one reacts with amino acids present in the fingerprint to form fluorescent derivatives.

Physical removal of the fingerprint deposit itself therefore renders many, if not all, conventional techniques inadequate. Examples of such situations are when the prints have been removed deliberately to avoid detections, where the prints have been removed through the effects of percussion/explosion or where the object comprising the print has been submersed in a liquid, such as water.

It has been observed that the small molecule disulfur dinitride, $S_2N_2$, is a suitable development agent for latent fingerprints (Kelly et al. 2008. Fingerprint and inkjet-trace imaging using disulfur dinitride. Chem. Commun. 6111-6113). Traditional generation of $S_2N_2$ has been achieved via thermal pyrolysis of purified $S_4N_4$ through silver wool. Although purified $S_4N_4$ has previously be shown to be an effective precursor molecule for yielding a high purity of $S_2N_2$ for fingerprint visualisation purposes, $S_4N_4$ is friction-sensitive and carries a risk of explosion if not handled correctly.

The present invention addresses one or more of the limitations of generating $S_2N_2$, in particular providing a much safer means of generating $S_2N_2$ for the purpose of visualising a print on an object.

Accordingly, in the first aspect of the present invention there is provided a method for the production of a metal halide adduct of $S_4N_4$ comprising the steps of: a) reacting $S_2Cl_2$ with gaseous ammonia in a dry solvent to produce crude $S_4N_4$; b) without purification, adding the crude $S_4N_4$ to a solution of metal halide in alcohol and stirring until no $S_4N_4$ remains; and c) obtaining the metal halide adduct of $S_4N_4$ by removal of the alcohol.

The term 'without purification' for the purpose of the present invention is understood in particular to mean there being no additional chemical and/or physical method(s), known to the skilled person, for improving the purity of crude $S_4N_4$, for example by recrystallisation.

The term 'removal of the alcohol' for the purpose of the present invention is understood to mean any suitable technique known to the skilled person, for example removal by filtration.

The Applicant has identified that a metal halide adduct of $S_4N_4$ can be substituted for $S_4N_4$ in a method for visualising fingerprints, and that such an adduct is much safer that $S_4N_4$ in such a method since such a product is not friction-sensitive and thus any risk of explosion is mitigated. In addition, the Applicant has devised a method for generation of such an adduct which does not require the $S_4N_4$ (generated in the first step of the method) to be purified prior to the subsequent steps of the method, thus also mitigating the risk of explosion during the method of preparation of the adduct. The Applicant has surprisingly and unexpectedly found that use of crude $S_4N_4$ (without purification) in the method does not interfere with the subsequent steps of the method, and indeed produces a product (metal halide adduct) which performs just as well in the fingerprinting method as purified $S_4N_4$ used in conjunction with sliver wool. The crude $S_4N_4$ obtained in the first step of the method can thus be used without any need for further purification prior to adding to a solution of metal halide in alcohol. The improved method of the first aspect of the invention provides a simple manufacturing process providing a yield of approximately 1:1 by weigh of metal halide adduct from crude $S_4N_4$, wherein the metal halide adduct can be used in a downstream method to generate $S_2N_2$ capable of obtaining high quality fingerprints in a fingerprint visualisation method. Advantageously, use of a metal halide adduct of $S_4N_4$ provides a less sensitive precursor material, relative to $S_4N_4$, therefore mitigating against the risk of friction sensitivity issues such as explosion. The use of the metal halide adduct produced by the method of the first aspect in a fingerprinting visualisation method is capable of generating high purity $S_2N_2$, instead of through the traditional approach involving the thermal pyrolysis of $S_4N_4$ through silver wool for development of latent fingerprints.

The metal of the $S_4N_4$ adduct may be selected from adducts of metals of groups 3 to 12 of the periodic table, also known as the transition or d-block elements. Preferably, the metal is selected from group 11, for example it is preferred that the metal is copper.

The $S_4N_4$ metal adduct comprises a halogen. Suitable halogens include fluorine (F), chlorine (Cl), bromine (Br) and iodine (I). The nature of the halogen may depend on the nature of the metal used and would be apparent to those skilled in the art. A preferred halogen is Br.

It is preferred that the metal halide adduct is $CuBr \cdot S_4N_4$.

Accordingly, in an embodiment of the first aspect of the present invention, there is provided a method wherein the metal halide is $CuBr_2$ and the metal halide adduct of $S_4N_4$ is $CuBr \cdot S_4N_4$. This feature provides the advantages of $CuBr \cdot S_4N_4$ having better ease of use and increased stability in terms of friction sensitivity, when compared to $S_4N_4$. Furthermore, $CuBr \cdot S_4N_4$ can be synthesised quickly (i.e. approximately 45 minutes) or, if preferable, synthesised over a longer duration (for example, up to three to four hours, or for longer durations such as overnight) with no detrimental effect in terms of the final reaction product. Furthermore, bulk $CuBr \cdot S_4N_4$ material is capable of storage in air with no evident decomposition observed over several months.

Alternatively, the metal halide is CuCl and the metal halide adduct is $CuCl \cdot S_4N_4$.

In an embodiment of the first aspect of the present invention, there is provided a method wherein the dry solvent is carbon tetrachloride or tetrachloroethylene. This feature provides the advantage of a suitable solvent to enable the production of crude $S_4N_4$ from $S_2Cl_2$, wherein the impurities present do not affect the ability to generate the metal halide adduct, and indeed to generate $S_2N_2$ from the metal halide adduct, such that good quality fingerprints can subsequently be obtained in a fingerprint visualisation method.

In an embodiment of the first aspect of the present invention, there is provided a method wherein the alcohol is methanol. This feature provides the advantage of a suitable solvent for dissolving crude $S_4N_4$ in order to obtain a metal halide adduct of $S_4N_4$, wherein the impurities present do not affect the ability of the metal halide adduct to generate $S_2N_2$, such that good quality fingerprints can subsequently be obtained in a fingerprint visualisation method.

It has been found that the reaction in the first step of the method is highly exothermic. It is therefore preferred that the reaction is conducted whilst being cooled.

Typically, the first method step is conducted at a temperature of less than about 100° C., for example from about 0° C. to about 80° C., preferably from about 0° C. to about 50° C., for example from about 0° C. to about 40° C.

Accordingly, in an embodiment of the first aspect of the present invention there is provided a method according wherein the first step is conducted at a temperature of less than about 100° C.

Typically, the second method step is conducted at a temperature of from about 40° C. to about 60° C., for example about 50° C.

Accordingly, in a further embodiment of the first aspect of the present invention, there is provided a method wherein the second step is conducted at a temperature of from about 40° C. to about 60° C.

Obtaining the metal halide adduct of $S_4N_4$ by removal of the alcohol, for example by filtration, can be achieved at ambient temperature.

Suitable methods of heating are well known in the art and include but are not limited to the use of an oil bath, heating plate or heating tape. If required during the first step, the reaction can be cooled using methods known in the art. Such methods include but are not limited to an ice/water bath, solid carbon dioxide, liquid nitrogen and electrical cooling methods.

In a second aspect of the present invention there is provided a method for visualising a print on an object comprising the steps of: a) placing within an apparatus: i) the object potentially comprising at least one print and ii) the metal halide adduct of $S_4N_4$ produced by the first aspect; b) heating the metal halide adduct of $S_4N_4$ under vacuum to produce $S_2N_2$ vapour; c) cooling the $S_2N_2$ vapour at or in proximity to the object to promote a phase change to solid $S_2N_2$: and d) heating the solid $S_2N_2$ back to $S_2N_2$ vapour to facilitate interaction of the $S_2N_2$ vapour with the object to visualise the print.

Thus, the present invention provides a use of a metal halide adduct of $S_4N_4$, obtained by the method of the first aspect of the present invention, for the visualisation of a print on an object. Preferably, use of $CuBr \cdot S_4N_4$ to produce $S_2N_2$ vapour for the visualisation of a print on an object is provided. The proposed use of $CuBr \cdot S_4N_4$ as a precursor material not only allows the efficiency and safety of the technique to be increased, but it also facilitates operational flexibility as the amount of precursor used per run may be varied (particularly increased) based on both the substrates type and treatment chamber size, without increasing the safety risk to a user, such as a forensic scientist, or indeed to the equipment, especially from risk of explosion.

The term 'prints' for the purpose of the present invention may be a fingerprint, ear print, lip print, palm print, foot print, ink print or shoe print. Preferably, the print is a fingerprint. As used herein, the term fingerprint encompasses thumb prints.

The term 'object' for the purpose of the present invention may be any object which may comprise a print to be visualised, such as a print on the surface of the object, and can be of any material on which a print can be retained. Examples of materials which may contain a print to be visualised include but are not limited to metal, paper, cardboard, wood, fabric, plastic, glass or a combination thereof. Suitable metals include but are not limited to iron, steel, brass, bronze, zinc, gold, silver, platinum, tin, copper, lead, nickel, chromium, titanium and aluminium and mixtures and alloys thereof. Suitable fabrics include but are not limited to cotton, linen, polyester, nylon and other man-made fabrics and mixtures thereof.

The method of the invention can be used to visualise a print on a variety of articles. Such articles include but are not limited to: weapons such as a gun, gun cartridge, ammunition, bullet, shell, knife, sword, bayonet, machete; parts of a building such as a window, door or lock; a vehicle; an article of furniture; a tool such as a hammer, screwdriver or crowbar; jewelry; electrical devices; electronic devices; a lock or key; bank notes; and a household article such as a kitchen knife.

This method of the second aspect of the present invention has been shown to offer a number of advantages over techniques currently used for visualising fingerprints. Firstly, using the metal halide adduct of $S_4N_4$, generated from $S_4N_4$ obtained without prior purification, has been shown to be effective in producing $S_2N_2$ vapour which is superior at developing fingerprints on certain materials, in particular metal objects, when compared to more conventional methods such as cyanoacrylate fuming. Secondly, it has been shown that DNA is unaffected by $S_2N_2$ treatment produced by the method of the second aspect, which is clearly an attractive feature from a crime scene evidence collection perspective. Thirdly, the method is particularly suitable for visualising prints that are not readily visible to the naked eye, such as latent prints. The method can be used to improve the visibility of a print that is at least in part visible to the naked eye.

However, perhaps most advantageously, the $S_2N_2$ produced by the method of the second aspect i.e. generated from $S_4N_4$ obtained without prior purification, has been shown to be highly adept at recovering different types of prints from a variety of materials and objects, in particular materials and objects that have been tampered with or undergone a force or treatment that may have rendered the print more difficult to recover or visualise with other visualisation techniques. For example, it has been found that the method can be used to visualise prints on surfaces that have been subjected to wetting, heat and/or friction. For example, the method can still be successful even if the object has been cleaned, submersed in water or been subjected to percussion and/or explosion. For example, the object comprising the print may be a used gun cartridge that has been subjected to the force and heat of firing the gun. The method of the invention can be used to visualise prints on objects that have been deliberately washed, for example by cleaning with a detergent. The method of the second aspect is particularly suitable for visualising prints on a metal surface, such as brass or stainless steel, which has been cleaned or washed.

Heating the metal halide adduct of $S_4N_4$ causes decomposition of the adduct, releasing $S_2N_2$ vapour. Once in the gaseous state the $S_2N_2$ has a high thermal energy. The heating temperature is selected so as to generate $S_2N_2$ vapour, but ideally the heating temperature is controlled to prevent the $S_2N_2$ vapour having excess thermal energy and to prevent the formation of undesirable by-products.

The temperature required must be sufficient to cause the adduct to decompose and release $S_2N_2$ vapour when heated and will depend on the metal used. Typically the temperature at which the metal halide adduct of $S_4N_4$ is heated is from about 100° C. to about 200° C., for example from about 155° C. to about 190° C., preferably 155° C. to about 170° C., and further preferably about 160° C. These temperatures are particularly suitable when $CuBr \cdot S_4N_4$ is used.

Investigations conducted suggested one possible preferred reaction condition was a heating temperature of 160° C. for 40 minutes to produce sufficient enough $S_2N_2$. Prolonged heating, intending to generate all the $S_2N_2$ from the $CuBr \cdot S_4N_4$ precursor was not shown to provide any significant benefits over the 40 minute heating phase. It was concluded, therefore, that heating of the precursor material should, for example, be maintained at 160° C. for 40 minutes to efficiently generate $S_2N_2$.

The thermal decomposition of $CuBr \cdot S_4N_4$ within a vacuum chamber provides the most effective way of employing this novel forensic technique. In the case of $CuBr \cdot S_4N_4$, the decomposition in vacuo results in the liberation of vapours that solidify as pale red films and colourless crystals when interacting with an intentionally cooled surface, analogous to the reaction products obtained from the traditional $S_4N_4$ thermal pyrolysis. These observations gave evidence for the generation of $S_2N_2$ from $CuBr \cdot S_4N_4$ adduct from a thermal decomposition pathway and in turn offered the potential to use these precursors as an alternative to $S_4N_4$ purified through silver wool in generating $S_2N_2$ in a more convenient, simple and safe fashion.

The metal halide adduct of $S_4N_4$ is typically heated from about 5 minutes to about 90 minutes, for example for from about 50 to about 70 minutes, such as for about 60 minutes.

Accordingly, In an embodiment of the second aspect of the present invention, there is provided a method wherein the metal halide adduct of $S_4N_4$ is heated to from about 160° C. to about 170° C.

The metal halide adduct of $S_4N_4$ can be heated using such methods that are known in the art. Suitable methods include but are not limited to the use of an oil bath, electrical heating means, heating plate or heating tape or heating means that are integral or internal to the apparatus in which heating is conducted.

The amount of the metal adduct of $S_4N_4$ to be heated depends on the size of the sample and also on the size of the apparatus in which the method of the invention is conducted. A suitable amount of the metal adduct may be from about 0.1 g to about 5 g, preferably about 0.1 g to about 1 g, and further preferably about 0.1 g to about 0.2 g.

Once produced, the $S_2N_2$ vapour is cooled. The $S_2N_2$ vapour may be cooled directly after it has been obtained by heating the metal adduct. This cooling step reduces the thermal energy of the vapour, and often results in the crystallisation of $S_2N_2$ (for example in the vicinity of the object). Without wishing to be bound by theory, this step thus has the effect of isolating or 'trapping out' solid $S_2N_2$ in the vicinity of the object placed within the apparatus proximal to the source of the cooling. The $S_2N_2$ vapour is typically cooled to a temperature of less than about 25° C., such as from about 0° C. to about 25° C., or even below about 0° C. such as about −5° C. For the cooling step, the $S_2N_2$ vapour is typically cooled for from about 30 minutes to about 2 hours, for example for about 1 hour.

Any suitable method of cooling may be used for the cooling step. Suitable methods are well known in the art and include but are not limited to a salt/ice bath, solid carbon dioxide, liquid nitrogen and electrical cooling methods e.g. a cooling element.

Accordingly, in an embodiment of the second aspect of the present invention, there is provided a method wherein the $S_2N_2$ vapour is cooled to a temperature of from about 25° C. to about 0° C.

After the $S_2N_2$ vapour has been cooled, the solid $S_2N_2$ is heated gently to allow interaction of $S_2N_2$ vapour with any print present on the object. It is thought that this heating can increase the thermal energy to a level which facilitates interaction of the $S_2N_2$ vapour with a fingerprint present on the object.

This step of heating the solid $S_2N_2$ typically involves heating to a temperature of from about 25° C. to about 65° C., such as about 30° C. for a period of from about 5 minutes to about 2 hours, for example from about 10 minutes to about 1 hour, for example for about 15 minutes or about 30 minutes. The period of this reheating step is typically not for the whole of the contact time of the $S_2N_2$ with the object.

Accordingly, in an embodiment of the second aspect of the present invention, there is provided a method wherein the solid $S_2N_2$ is heated to generate $S_2N_2$ vapour at a temperature of from about 25° C. to about 50° C.

With regards to heating of the solid $S_2N_2$, this can be achieved for example via either i) removing the cooling effect such that the solid $S_2N_2$ gently heats to $S_2N_2$ vapour at ambient temperature, or ii) heating the solid $S_2N_2$, such that the resulting $S_2N_2$ vapour reaches above ambient temperature. Any suitable heating method may be used for the gentle heating step. Suitable methods are well known in the art and include but are not limited to the use of an oil bath, electrical heating means, heating plate or heating tape or heating means such as a heating element that is integral or internal to the apparatus in which heating is conducted. A cooling element associated with the cooling step may also function as a heating element for heating $S_2N_2$.

The object comprising the print to be visualised is typically contacted with the $S_2N_2$ for sufficient time to visualise the print, for example for at least about 1 to 15 minutes. Preferably, the object is contacted with the $S_2N_2$ vapour for from about 30 minutes or 1 hour or 2 hours to about 36 hours, for example from about 8 hours to about 24 hours or overnight, for example about 12 hours. During the contact time, the $S_2N_2$ vapour polymerises on the surface of the object comprising the print. Polymerisation of the $S_2N_2$ results in the visualisation of the print. Typically, a dark blue/black polymer forms only where the print has contacted the surface. Under certain lighting angles the polymer may appear to be gold in colour.

Accordingly, in an embodiment of the second aspect of the present invention, there is provided a method wherein the object comprising a print is contacted with the $S_2N_2$ vapour for at least 1 minute, or at least 15 minutes, for example approximately 5 minutes, 15 minutes, 1 hour, or 2 hours, or alternatively overnight, such as for from about 8 hours to about 12 hours.

The use of a vacuum system mitigates against aerial hydrolysis and increases vapour pressure, allowing $S_2N_2$ to enter the vapour state and diffuse, ultimately helping to induce polymerisation.

For the method of the second aspect, the step of heating the metal halide adduct to generate $S_2N_2$ vapour is conducted at sub-atmospheric pressure under vacuum, such as at a pressure of from about $1.33\times10^{-6}$ Pa ($1\times10^{-9}$ mm/Hg) to about 133 Pa (1 mmHg). This vacuum may be static or dynamic.

Similarly, the step of contacting the object comprising the print with $S_2N_2$ vapour is conducted at sub-atmospheric pressure under vacuum, such as at a pressure of from about $1.33\times10^{-6}$ Pa ($1\times10^{-9}$ mm/Hg) to about 133 Pa (1 mmHg). This vacuum may be static or dynamic.

Accordingly, in an embodiment of the second aspect of the present invention, there is provided a method wherein the vacuum is at a pressure of from about $1.33\times10^{-6}$ Pa ($1\times10^{-9}$ mm/Hg) to about 133 Pa (1 mmHg).

In particular, a dynamic vacuum is applied during heating of the metal halide adduct. This approach has been shown to be more effective, compared to a static vacuum, and is thought to aid sublimation of the metal halide adduct as well as increasing the vapour pressure of the generated $S_2N_2$. The vacuum within the system effectively weakens under a static atmosphere as the vapour pressure of the decomposition $S_2N_2$ vapours take effect. Furthermore, equilibrium exists in the head space above the solid metal halide adduct precursor in which some amount of reversibility is occurring. Where a dynamic vacuum is provided, decomposition vapours can be directed towards the object comprising at least one print through the action of the constant vacuum pull.

Upon heating the solid $S_2N_2$, a static vacuum can be applied to enable the resulting vapour to interact with the surface of the object, thereby developing latent fingerprints of interest.

A vacuum is obtained using approaches known to the skilled person, for example using a vacuum pump to provide a vacuum within a sealed environment. Once a vacuum has been established, the means by which the vacuum was obtained can optionally be switched off so that the chamber remains under static vacuum. For example, the vacuum pump may be operating while the metal halide adduct of $S_4N_4$ is heated and then turned off and the vacuum maintained (as a static vacuum) during the $S_2N_2$ contacting step.

Any suitable recording techniques may be used to preserve information obtained from a visualised print. Thus, the method of the invention may also include the step of recording an image of the visualised print, for example by photography.

It is also envisaged that the visualised print can be further enhanced by viewing under polarized light or by the use of sources of light within a particular frequency range such as ultra-violet light or infra-red light by the application of digital imaging processing.

Once visualised, the print can be analysed, for example by comparing the visualised print to another print, such as a print obtained from an alternative source or a print from a record or library.

Therefore, the present invention also provides for a visualised print obtained by the second aspect of the present invention, and use of the visualised print obtained by the second aspect of the present invention.

In accordance with the second aspect there is also provided the use of $CuBr \cdot S_4N_4$ for the visualisation of a print on a surface.

Furthermore, the present invention provides for use in pellet form of the metal halide adduct of $S_4N_4$, obtained by the method of the first aspect, for the visualisation of a print on a surface. This provides the advantages of not requiring careful weighing and transfer. Pelletisation can be achieved using a die/press arrangement that allowed the application of pressure via hydraulic press as would be understood by the skilled person.

Preferably, the use of a metal halide adduct of $S_4N_4$ such as $CuBr \cdot S_4N_4$ in pellet form to produce $S_2N_2$ vapour for the visualisation of a print is provided.

It is envisaged that the pellet comprises a metal halide adduct of $S_4N_4$ and an excipient. Suitable excipients would be known to those skilled in the art. Studies suggest a low release time is favoured by a high surface area and low width for the pellets employed. The pellet may be approximately 20% by weight metal halide adduct of $S_4N_4$, for example 22%. However, a high percentage content of precursor can be contained within the pellets. Therefore, the pellet may be, for example, approximately 60-70% by weight metal halide adduct of $S_4N_4$, for example 66%. In particular, the metal halide adduct of $S_4N_4$ is $CuBr \cdot S_4N_4$. The pellet excipient may comprise micro-crystalline cellulose. Alternatively, the pellet excipient may comprise polyvinylpyrrolidone.

In a third aspect of the present invention, there is provided an apparatus for the method for visualising a print on an object comprising: a first chamber comprising a heating element for heating the metal halide adduct of $S_4N_4$, produced by the method of the first aspect, to produce $S_2N_2$ vapour; a second chamber in communication with the first chamber and in which an object potentially comprising at least one print can be arranged, the second chamber comprising a cooling element for cooling $S_2N_2$ vapour produced from the first chamber; and a vacuum pump in communication with the second chamber; wherein in use the $S_2N_2$ vapour is cooled in the second chamber at or proximal to the object, to facilitate interaction between the $S_2N_2$ vapour and the object.

Thus, the apparatus of the third aspect is capable of undertaking for the method of the second aspect of the present invention, wherein a metal halide adduct of $S_4N_4$ obtained by the method of the first aspect of the present invention is used for the visualisation of a print on the surface of an object.

As used herein, referring to heating or cooling refers to the temperature at which the heating element and/or cooling element is set or maintained. It will be appreciated that this may be different to the internal temperature within the apparatus in which the method of the invention is conducted or the temperature of the sample.

Typically the object is contacted with the $S_2N_2$ vapour in the second chamber of the apparatus.

The second chamber is suitable for containing a vacuum (either a dynamic vacuum or a static vacuum). An example of a lab scale apparatus may comprise a second chamber of up to 10 litres, or alternatively from about 10 to about 50 litres, for example 20 litres.

It will be appreciated that the apparatus must be able to maintain the vacuum, for example but not limited to inside the second chamber, for the desired period of time in accordance with the method for visualising a print on a surface.

Optionally, when undertaking the method of the second aspect of the invention, sample objects can be fixed in place within the apparatus of the third aspect of the invention using appropriate fixing methods. Suitable fixing means include but are not limited to double-sided tape, Velcro, or clipped fastenings. This arrangement allows the object to be located at or proximal to where the $S_2N_2$ vapour is to be cooled.

Preferably, the heating element in the first chamber comprises a heatable base, for example comprising at least one heating element together with a temperature sensor. This configuration allows the heating block to quickly reach the required temperature with minimal overshoot, and for this temperature to be maintained accurately. Furthermore, heating provides the freshly generated $S_2N_2$ vapour with enough thermal energy to migrate to the second chamber. At least one heating element may be a high performance ceramic heating element. The sensor may be a high accuracy platinum resistance (PT100) sensor. Preferably, the heating element is processor controlled to ensure a high degree of control accuracy.

Preferably, the cooling element comprises a coolable base plate, for example a coolable base plate controlled by a bank of solid state thermoelectric modules (e.g. solid state heat pumps such as Peltier devices) together with a temperature sensor. This feature ensures a rapid cooling capability with a high degree of temperature control. The sensor may be a high accuracy platinum resistance (PT100) sensor.

To aid cooling of the $S_2N_2$ vapour, the apparatus may also comprise a closed circuit liquid cooling system, to remove heat from the cooling element. The closed circuit liquid cooling system may utilise a high performance machined copper Liquid Cooled Plates (LCP).

Furthermore, the apparatus may comprise a fan-cooled radiator, to dissipate waste heat.

With regards to the step of heating the solid $S_2N_2$, as described in the second aspect of the present invention, this can be achieved via the apparatus of, the third aspect via either i) removing the cooling effect, for example by switching off the cooling element such that the solid $S_2N_2$ gently heats to generate $S_2N_2$ vapour at ambient temperature, or ii) the cooling element is (also) capable of heating the solid $S_2N_2$ such that resulting $S_2N_2$ vapour is formed, for example heating to just above ambient temperature.

Preferably, the second chamber may communicate with the first chamber via a valve. Further preferably, the second chamber may communicate with the vacuum pump via at least one valve, for example via at least one value and a filter chamber. The filter chamber may connect to the main chamber through a ball value and to the vacuum pump through a ball valve. The filter chamber may accommodate an activated charcoal filter for removal of any precursor-generated particles. Alternatively, the second chamber may communicate with the vacuum pump via two valves and a filter chamber, the filter chamber located intermediate to the two valves.

Preferably, the second chamber may be in communication via a valve with an environment external to the apparatus, for example via a valve and vent filter. This feature allows air to be drawn into the apparatus for flushing purposes.

Preferably, one or more values of the apparatus may be a ball valve. Further optionally, one or more valves may be operated by an electric motor actuator. Furthermore, one or more of the valves may be controlled by a control system.

Preferably, the first chamber and/or second chamber may comprise a viewing window, to aid viewing of the precursor and/or see inside the chamber during the reaction to enable visual inspection of the object, and the surface comprising a print. The apparatus may further comprise a lamp, such as a lamp capable of providing white light to the inside of the chamber where the object and $S_2N_2$ vapour are contained during operation of the apparatus, wherein the lamp is a moveable lamp mounted relative to the first chamber and/or second chamber window, which can be positioned as required for viewing objects placed within.

Preferably, the first chamber and/or second chamber may further comprise a door, for example a door with an interlock. This feature prevents opening once the apparatus is running. At least one window may be arranged in the door or the first chamber and/or second chamber.

The notion of pelletisation or containment of the precursor in a manner than can be employed within the known apparatus and protocol is desirable, as the storage and utilisation would be rendered substantially easier.

Preferably, to assist with simplicity of use, the apparatus may be fully processor controllable by a man-machine interface The invention will now be described with reference to the following non-limiting examples and figures, in which:

Figure 1:
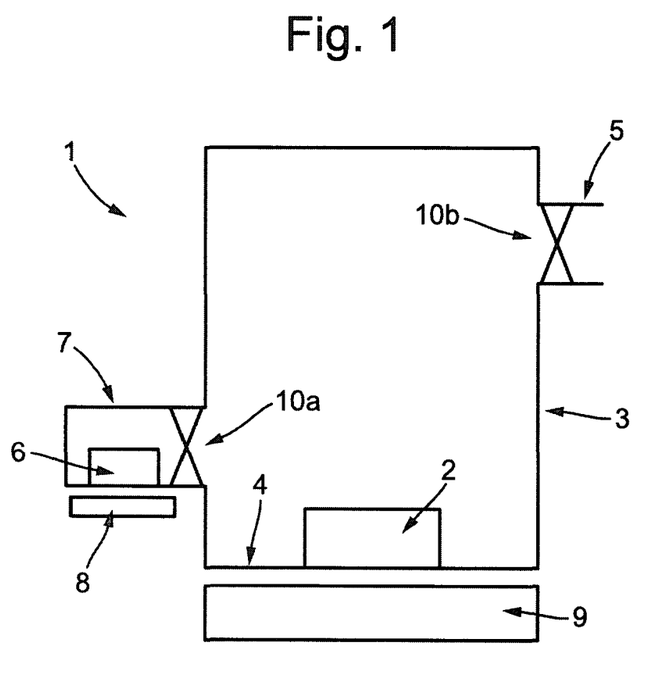
FIG. 1—is an example of a laboratory scale apparatus used to conduct a method of the present invention.

As shown in FIG. 1, the object (2) comprising the print to be visualised can be placed in an apparatus (1) comprising a chamber (3) with a surface (4) suitable for holding the object comprising a print.

In the apparatus (1) shown, the chamber is connected to a vacuum pump (not shown) via a tube (5).

CuBr·S$_4$N$_4$ (6) is placed in a side arm (7) connected to the chamber (3). The side arm (7) and the tube (5) are positioned such that when the CuBr·S$_4$N$_4$ (6) is heated via a heating element (8) to produce S$_2$N$_2$ vapour, the vapour enters the chamber (3) at a point such that the vapour subsequently cools to form solid S$_2$N$_2$ proximal to the cooling element (9) i.e. the S$_2$N$_2$ vapour is not immediately removed by the vacuum pump which is typically on whilst the CuBr·S$_4$N$_4$ (6) is heated. After cooling, the solid S$_2$N$_2$ is converted via heating to S$_2$N$_2$ vapour in order to contact the object (2) comprising a print. Upon completing the duration in which the S$_2$N$_2$ vapour contacts the object (2), the vapour is removed from the chamber (3) via the tube (5) connected to the vacuum pump.

When a vacuum is to be used in the present invention, the apparatus (1) must be capable of holding a vacuum. Vacuum taps (10a, 10b) are provided, which can be closed to maintain a static vacuum inside chamber (3). Thus, the interior of the chamber (3) can be maintained under vacuum even after the vacuum pump has been turned off. A suitable chamber (3) would be able to maintain a pressure of from about $1.33 \times 10^{-6}$ Pa ($1 \times 10^{-9}$ mm/Hg) to about 133 Pa (1 mmHg) without the assistance of a vacuum pump.

In use, object (2) to be treated for latent fingerprints is arranged inside chamber (3) with a small quantity (approx. 0.5-1 g) of precursor CuBr·S$_4$N$_4$ (6) in crystal form, placed in the side arm (7) connected to the chamber (3). The chamber (3) is then evacuated by a vacuum pump via tube (5), connected to the other side of the chamber, while a cooling element (9) associated with the base of chamber (3) is used to create a chilled area.

CuBr·S$_4$N$_4$ (6) in the side arm (7) is heated at a temperature of 160° C. under a vacuum of about 13 Pa (0.1 mmHg).

During the step of heating of CuBr·S$_4$N$_4$ (6), the adduct decomposes and releases S$_2$N$_2$ vapour. The atmosphere in the chamber (3) containing the object. (2) comprising a print is cooled using a cooling element (9) at the same time as the side arm (7) is heated, with the resultant effect that the S$_2$N$_2$ vapour is cooled upon entering the chamber (3).

After heating CuBr·S$_4$N$_4$ (6) for sufficient time to release enough S$_2$N$_2$ vapour for condensing on the cooling element (9), the vacuum taps (10a, 10b) are closed and a static vacuum is maintained.

The cooling effect provided by the cooling element (9) is then stopped, and the chamber (3) is then heated to about 30° C. for between 5 minutes and 2 hours, for example for about 15 minutes.

The chamber (6) containing the object (2) comprising a print to be visualised can be then left to develop for at least 15 minutes.

Fingerprint development is observed as S$_2$N$_2$ vapour polymerises on the object (2) being treated and when maximum contrast between ridges and background is obtained excess vapour is vented from the chamber (3) and the marks photographed.

Various modifications to the apparatus (1) can be made as will be apparent to those skilled in the art. For example, the metal halide adduct of S$_4$N$_4$ may be held in containment material in which containment material includes: a mesh; a stainless steel mesh; an ampule; a metal tray with a removable seal; a paper sachet; and/or a plastic container. Other means apparent to the skilled person could be envisaged for heating the metal halide adduct of S$_4$N$_4$, for example using heating tape around a containment material in which the metal halide adduct of S$_4$N$_4$ may be held, or alternative heating means surrounding the whole metal halide adduct of S$_4$N$_4$ to ensure that no cold spots develop which allows premature solidification of the S$_2$N$_2$ vapour. Furthermore, other means could be envisaged for cooling the chamber (3), for example an ice/water bath or 'cold-finger' arrangement. The apparatus (1) may be a man-portable device. Furthermore, the apparatus (1) may be built at least predominantly of stainless steel. The size of the chamber (3) can be varied according to the desired application. For example, chamber (3) could provide for a relatively small enclosed volume to specifically deal with smaller items such as cartridge casings.

The present invention is illustrated by the following non-limiting Examples.

Example 1: Synthesis of Crude Tetrasulfur Tetranitride (S$_4$N$_4$)

Sulfur (I) dichloride, S$_2$Cl$_2$ (50.0 ml, 84.00 g, 0.62 moles) and dry carbon tetrachloride (1400 cm$^3$) were placed into a two litre, three necked, round bottomed flask. A paddle stirrer was inserted through the main neck of the flask and open-end gas inlet tubes were inserted through the remaining necks. While the mixture was stirred briskly (ca. 500 rpm), a steady stream of chlorine gas was passed directly into the solution, until a distinct green layer of chlorine was clearly visible in the headspace. The flow of chlorine was then stopped and a flow of nitrogen was passed through the solution until the excess chlorine was removed. The round bottomed flask was then immersed into a water/ice bath, and ammonia gas was passed through the stirred solution, keeping the temperature below 50° C. Levels of carbon tetrachloride were maintained throughout the reaction. After approximately 3 hours, the reaction mixture was golden-poppy in colour and pH>8, at this point the reaction was ceased. The reaction mixture was carefully filtered, under vacuum, on a large Buchner funnel. The damp solid material collected was vigorously slurried with de-ionised water (1000 cm$^3$) for 5-10 minutes and the remaining undissolved solid allowed to dry, in air, for 2 days. This crude form of the product was then used for the subsequent synthesis of the CuBr·S$_4$N$_4$ adduct. IR: υ 922, 688, 539 cm$^{-1}$.

Example 2: Synthesis of Crude Tetrasulfur Tetranitride (S$_4$N$_4$)

Sulfur (I) dichloride, S$_2$Cl$_2$ (85 cm$^3$, 142.80 g, 1.054 moles) and tetrachloroethylene (2100 cm$^3$) were placed into a three litre, three necked, round bottomed flask. A paddle stirrer was inserted through the main neck of the flask and open-end gas inlet tubes were inserted through the remaining necks. While the mixture was stirred briskly (ca. 500 rpm), a steady stream of chlorine gas was passed directly into the solution, until a distinct green layer of chlorine was clearly visible in the headspace. The flow of chlorine was then stopped and a flow of nitrogen was passed through the solution until the excess chlorine was removed. The round bottomed flask was then immersed into a water/ice bath, and ammonia gas was passed through the stirred solution, keeping the temperature below 50° C. Levels of tetrachloroethylene were maintained throughout the reaction. After approximately 3 hours, the reaction mixture was golden-poppy in colour and pH>8, at this point the reaction was ceased. The reaction mixture was carefully filtered, under vacuum, on a large Buchner funnel. The damp solid material collected was vigorously slurried with de-ionised water (2000 cm$^3$) for 5-10 minutes, then washed with diethyl ether (ca. 50 cm$^3$), and the remaining undissolved solid allowed to dry, in air, for 2 days. This crude form of the product (ca. 50 g) was then used for the subsequent synthesis of the CuBr·S$_4$N$_4$ adduct. IR: υ 922, 688, 539 cm$^{-1}$.

Example 3: Synthesis of CuBr·S$_4$N$_4$

In a round-bottomed flask, CuBr$_2$ (6.059 g, 0.027 moles) was dissolved in methanol (120 cm$^3$) and non-purified S$_4$N$_4$ (5.002 g, approx 0.027 moles) obtained via the process of either Example 1 or 2 was added. The flask was sealed with a stopper and stirred at 50° C. for 45 minutes until no solid S$_4$N$_4$ remained. The resulting anthracite-black crystals of CuBr·S$_4$N$_4$ were collected via vacuum filtration and washed with methanol (3×50 cm$^3$), and after drying stored in sample vials in air. Typical yield=6.410 g (72%). Anal. Calcd. for CuBr·S$_4$N$_4$: N=17.1%; Found: N=17.1%. IR: υ 910, 694, 535 cm$^{-1}$.

Example 4: S$_2$N$_2$ Synthesis and Sample Treatment

Samples were pre-loaded into the development ('treatment') chamber using appropriate fixing methods (double-sided tape, Velcro, or clipped fastenings). The treatment chamber was sealed using the rubber O-ring gasket to join the two halves of the assembly. A B32 ground-glass head unit was then attached through the central opening of the treatment chamber, ensuring all joints and taps were well greased. The chamber was placed into a deep walled container/dish acting as a cooling bath and then evacuated at ca. 0.1 mm/Hg for approximately 1 hour.

The side-arm containing CuBr·S$_4$N$_4$ (0.6 g, 1.83 mmol) was then attached, again ensuring the B19 ground-glass joint was well greased, and the Isopad S45 heating tape, connected to an Isopad ML10 temperature controller, was placed around the majority of the side-arm (allowing only the bottom 1 inch to be uncovered). The Young's tap was then opened, allowing the side-arm to be evacuated for a further 30 mins. During this time, salt/ice was added to the container that the treatment chamber was rested in, so that the effective temperature was approximately −5° C. or below.

The heating tape was then switched on and allowed to establish a temperature of approximately 180° C. (ca. 5 min). When this point was reached, a pre-heated oil bath at 160° C. was raised to submerge the lower portion of the side-arm that was not directly heated by the heating tape.

The CuBr·S$_4$N$_4$ was heated in this fashion for approximately 50-60 mins, until its initial crystalline black appearance had changed to a dull grey/green colour. After this point, the Young's tap was closed along with the main vacuum tap (ensuring a static vacuum), the entire setup removed from the salt/ice bath and the base gently warmed to ca. 30° C. for 15 mins to allow the isolated S$_2$N$_2$ to enter the vapour state within the chamber.

Observation of samples within the chamber allowed appropriate development time to be recognised. Routinely, samples were not left exposed to S$_2$N$_2$ for longer than 24 hours. Removal of samples from the chamber was simply achieved by opening the vacuum tap to release the vacuum and careful dismantling of the two chamber halves to allow samples to be retrieved.

Typically, after the visualisation of the print, the object can be stored under normal atmospheric conditions. However, optimum conditions for storage would depend on the nature of the material that the object comprised.

If the object is metal then it is preferred that it is stored under conditions which prevent oxidation or corrosion effects, for example under dry, oxygen free conditions. The exact condition would depend on the reactivity of the metal with air and would be apparent to those skilled in the art.

Preferred storage conditions include an inert dry atmosphere, typically at room temperature or below, such from about −20° C. to about 20° C., for example from about 0° C. and 10° C., and that is optionally dark.

Example 5: Visualisation of a Print on Brass

A fingerprint was deposited on the a brass object and left for several hours before being washed off using water, then acetone, and finally buffed and dried to a polish with tissue paper. A photograph of the surface of the object on which the print had been applied after the washing and polishing steps viewed under an optical microscope at 10× magnification is shown in FIG. 2A.

The brass object was then subjected to a method as set out in Example 4. FIG. 2B shows the surface of the object after it was subjected to the method of Example 4 viewed under an optical microscope at 10× magnification.

Figure 2A:
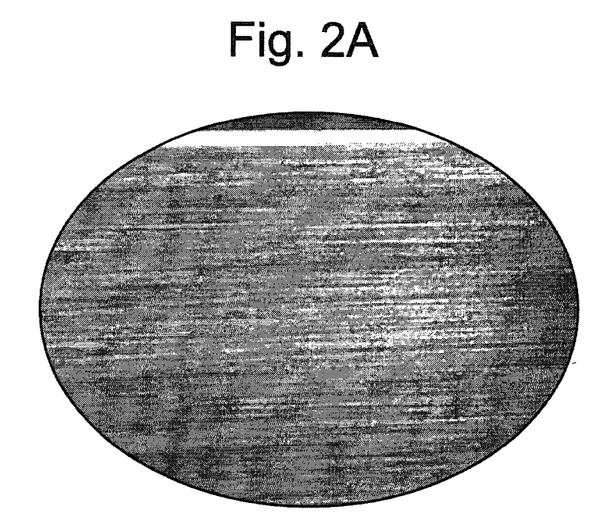
FIG. 2A—is a photograph of a print on a brass surface viewed under an optical microscope at 10× magnification before visualisation using the method of the present invention.
Figure 2B:
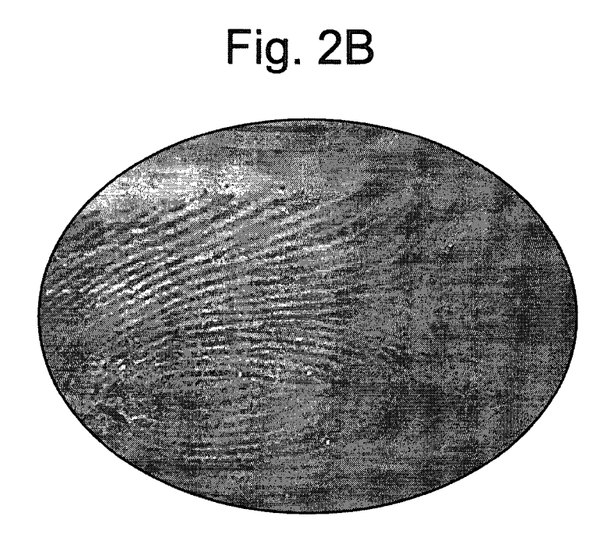
FIG. 2B—is a photograph of a print on a brass surface viewed under an optical microscope at 10× magnification after visualisation using the method of Example 4.

Comparison of FIGS. 2A and 2B shows that the method of the present invention is effective to visualise prints that are not otherwise visible to the naked eye or under standard magnification, such as 10× magnification.

It will be understood that the present invention has been described above purely by way of example, and modification of detail can be made within the scope of the invention. Each feature disclosed in the description, and (where appropriate) the claims and drawings may be provided independently or in any appropriate combination.

Moreover, the invention has been described with specific reference to fingerprint visualisation. It will be understood that this is not intended to be limiting and the invention may be used more generally. For example, the invention may be used more generally in the forensic fields, and may be used in other chemical applications. Additional applications of the invention will occur to the skilled person.

The invention claimed is:

1. A method for production of a metal halide product of S$_4$N$_4$ comprising the steps of:
    a. reacting S$_2$Cl$_2$ with gaseous ammonia in a dry solvent to produce crude S$_4$N$_4$;
    b. without purification, adding the crude S$_4$N$_4$ to a solution of metal halide in alcohol and stirring until no S$_4$N$_4$ remains; and
    c. obtaining the metal halide product of S$_4$N$_4$ by removal of the alcohol.

2. The method of claim 1, wherein the metal halide is CuBr$_2$, and the metal halide product of S$_4$N$_4$ is CuBr·S$_4$N$_4$.

3. The method of claim 1, wherein the dry solvent is carbon tetrachloride or tetrachloroethylene.

4. The method of claim 1, wherein the alcohol is methanol.

5. The method of claim 1, wherein step (a) is conducted at a temperature of less than about 100° C.

6. The method of claim 1, wherein step (b) is conducted at a temperature of from about 40° C. to about 60° C.

7. A method for visualising a print on an object comprising
    a. placing within an apparatus:
        i. the object potentially comprising at least one print; and
        ii. a metal halide product of S$_4$N$_4$ produced by a process comprising:

reacting $S_2Cl_2$ with gaseous ammonia in a dry solvent to produce crude $S_4N_4$;

without purification, adding the crude $S_4N_4$ to a solution of metal halide in alcohol and stirring until no $S_4N_4$ remains; and obtaining the metal halide product of $S_4N_4$ by removal of the alcohol;

b. heating the metal halide product of $S_4N_4$ under vacuum to produce $S_2N_2$ vapour;

c. cooling the $S_2N_2$ vapour at or in proximity to the object to promote a phase change to solid $S_2N_2$; and d. heating the solid $S_2N_2$ back to $S_2N_2$ vapour to facilitate interaction of the $S_2N_2$ vapour with the object to visualise the print.

8. The method of claim 7, wherein, in step (b), the metal halide product of $S_4N_4$ is heated to from about 160° C. to about 170° C.

9. The method of claim 7, wherein, in step (c), the $S_2N_2$ vapour is cooled to a temperature of from about 25° C. to about 0° C.

10. The method of claim 7, wherein, in step (d), the solid $S_2N_2$ is heated to generate $S_2N_2$ vapour at a temperature of from about 25° C. to about 50° C.

11. The method of claim 7, wherein the object is contacted with the $S_2N_2$ vapour for at least 1 to 15 minutes.

12. The method of claim 7, wherein the vacuum is at a pressure of from about $1.33 \times 10^{-6}$ Pa to about 133 Pa.

13. The method of claim 7, wherein, in step (b), the metal halide product of $S_4N_4$ is heated to from about 155° C. to about 170° C.

14. The method of claim 7, wherein, in step (c), the $S_2N_2$ vapour is cooled to a temperature of from about 25° C. to about −5° C.

15. The method of claim 7, wherein, in step (d), the solid $S_2N_2$ is heated to generate $S_2N_2$ vapour at a temperature of from about 25° C. to about 65° C.

16. The method of claim 1, further comprising forming at least a part of the metal halide product of $S_4N_4$ into a pellet.

17. The method of claim 16, wherein an excipient is provided when forming the at least the part of the metal halide product of $S_4N_4$ into the pellet.

18. The method of claim 17, wherein the excipient comprises microcrystalline cellulose or polyvinylpyrrolidone.

19. A method for visualising a print on an object comprising a. placing within an apparatus:
   i. the object potentially comprising at least one print; and
   ii. a metal halide product of $S_4N_4$;

b. heating the metal halide product of $S_4N_4$ under vacuum to produce $S_2N_2$ vapour;

c. cooling the $S_2N_2$ vapour at or in proximity to the object to promote a phase change to solid $S_2N_2$; and d. heating the solid $S_2N_2$ back to $S_2N_2$ vapour to facilitate interaction of the $S_2N_2$ vapour with the object to visualise the print.

* * * * *